(12) United States Patent
Abboud et al.

(10) Patent No.: US 8,297,108 B2
(45) Date of Patent: Oct. 30, 2012

(54) MESH LEAK DETECTION SYSTEM FOR A MEDICAL DEVICE

(75) Inventors: Marwan Abboud, Pierrefonds (CA); Dan Wittenberger, L'ile Bizard (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 178 days.

(21) Appl. No.: 12/767,012

(22) Filed: Apr. 26, 2010

(65) Prior Publication Data

US 2010/0204687 A1 Aug. 12, 2010

Related U.S. Application Data

(63) Continuation of application No. 11/476,405, filed on Jun. 28, 2006, now Pat. No. 7,716,966.

(51) Int. Cl.
*G01M 3/00* (2006.01)
(52) U.S. Cl. .................................................. 73/40.5 R
(58) Field of Classification Search ........................ None
See application file for complete search history.

(56) References Cited

U.S. PATENT DOCUMENTS

| 4,790,968 | A | * | 12/1988 | Ohkawa et al. | 264/104 |
| 4,921,484 | A | | 5/1990 | Hillstead | |
| 6,057,689 | A | | 5/2000 | Saadat | |
| 6,761,714 | B2 | | 7/2004 | Abboud et al. | |
| 6,826,948 | B1 | | 12/2004 | Bhatti et al. | |
| 7,097,643 | B2 | | 8/2006 | Cornelius et al. | |
| 2004/0243119 | A1 | * | 12/2004 | Lane et al. | 606/21 |

FOREIGN PATENT DOCUMENTS

CA 2361098 A1 7/2000
CA 2555922 A1 7/2000

* cited by examiner

*Primary Examiner* — Peter Macchiarolo
*Assistant Examiner* — Alex DeVito
(74) *Attorney, Agent, or Firm* — Christopher & Weisberg, P.A.

(57) ABSTRACT

The present invention provides a surgical device including an elongate body defining a fluid flow path therethrough. An expandable element may be coupled to the elongate body and placed in fluid communication with the fluid flow path. Moreover, the surgical device may include a first leak detection element at least partially surrounding a portion of the expandable element, and a second leak detection element may be provided in fluid communication with the fluid flow path. In addition, a console may be provided, where the console may be in communication with the first and second leak detection elements. Further, a supply of cryogenic fluid as well as a vacuum source may be provided in fluid communication with the fluid flow path.

4 Claims, 2 Drawing Sheets

MESH LEAK DETECTION SYSTEM FOR A MEDICAL DEVICE

CROSS-REFERENCE TO RELATED APPLICATION

This application is a continuation of pending utility patent application Ser. No. 11/476,405, filed Jun. 28, 2006, the entirety of which is incorporated herein by reference.

STATEMENT REGARDING FEDERALLY SPONSORED RESEARCH OR DEVELOPMENT n/a

FIELD OF THE INVENTION

The present invention relates to surgical devices, and more particularly to minimally invasive surgical systems employing fluid circulation.

BACKGROUND OF THE INVENTION

Surgical devices configured for minimally invasive surgery are rapidly becoming the tools of choice for many surgical procedures. Not only do these devices provide an alternative to more invasive surgical tools and procedures, but they have also fostered the development of entirely new procedures.

Devices including highly flexible catheters, as well as rigid and semi-flexible probes have received increased attention in recent years and continue to be refined for cardiovascular, pulmonary, urogenital, and other applications. Devices for each of these applications present different technology and material challenges. Angioplasty catheters, for example, can require fluid-tight passages or channels for circulating a cooling fluid (liquid or gas) through a catheter to cool an electrosurgical structure, such as radio frequency ablation electrode, to prevent overheating of the electrode or of surrounding tissue. Similarly, a cooling or cryogenic fluid can be reduce the temperature of a structure, such as an ablation surface, to a therapeutic temperature. Some cooling fluids, however, can be harmful or fatal to the patient if they unintentionally escape from the surgical device.

Although careful fabrication techniques, quality materials, and thorough testing can reduce the chances of cooling fluid leakage, it would be desirable to provide additional system features that further minimize the occurrence of leaks; and should a leak occur, provide features that detect cooling fluid loss or escape immediately so that use of the surgical device can be terminated and patient remediation efforts can be undertaken if required.

SUMMARY OF THE INVENTION

The present invention advantageously provides a system including a surgical device, where the surgical device may include an elongate body defining a fluid flow path therethrough. An expandable element may be coupled to the elongate body and placed in fluid communication with the fluid flow path. Moreover, the surgical device may include a first leak detection element at least partially surrounding a portion of the expandable element, where the first leak detection element may include an electrically conductive mesh. A second leak detection element may be provided in fluid communication with the fluid flow path, and electrically isolated from the first leak detection element. In addition, a console may be provided, where the console may be in communication with the first and second leak detection elements. Further, a supply of cryogenic fluid as well as a vacuum source may be provided in fluid communication with the fluid flow path.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

In the discussion which follows, "surgical device" is intended to encompass any surgical implement used in association with human or animal medical treatment, diagnosis, study, or analysis. More particularly, a surgical device is intended to encompass any implement or portion thereof that is entirely or partially inserted into a human or animal body by any means of entry, such as through a natural body orifice, an incision, or a puncture. The term surgical device is not intended to connote a limitation to treatment of a single body system, organ, or site.

As used herein, the term "fluid" is intended to encompass materials in a liquid state, a gas state, or in a transition state between liquid and gas, and liquid and solid. The fluid can be a "cryogenic fluid" capable of reaching or creating extremely cold temperatures well below the freezing point of water, such as below minus 20 degrees Centigrade; a "cooling fluid" that does not reach or create temperatures below the freezing point of water; a fluid capable of transferring heat away from a relatively warmer structure or body tissue; a fluid capable of transferring heat to a relatively cooler structure or body tissue; a fluid at or capable of creating a temperature between the freezing and boiling points of water; and a fluid at or capable of reaching or creating a temperature above the boiling point of water.

A "fluid path" as used herein is intended to encompass any boundary, channel or guide through which a fluid can travel. It can include concentrically disposed catheters, multi-lumen catheters, or a single loop of tubing within a sheath. The fluid path can also include connectors and valves, as well as passages in support equipment, such as the console disclosed herein.

Figure 1:
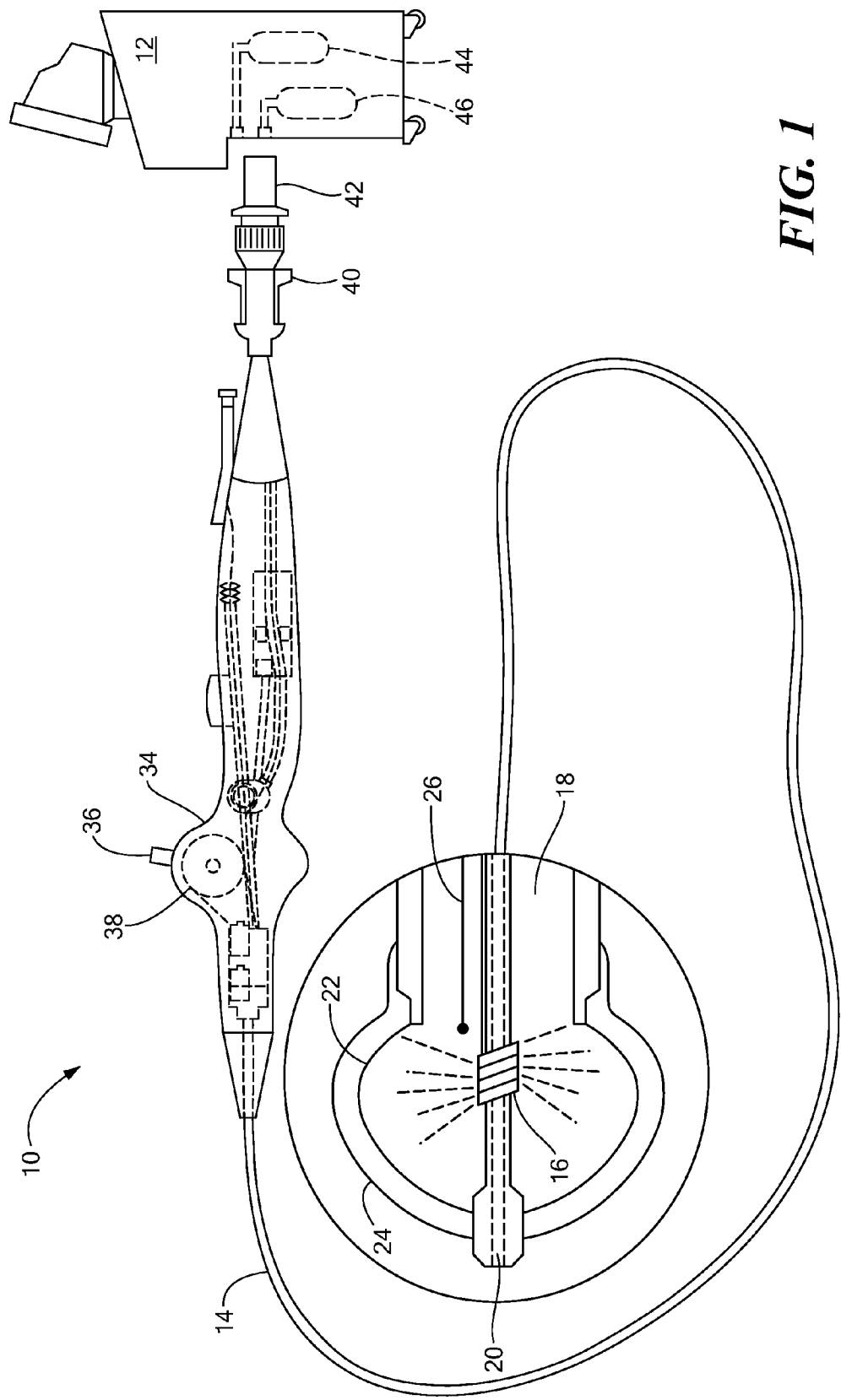
FIG. 1 illustrates an embodiment of a surgical device in accordance with the present invention.
Figure 2:
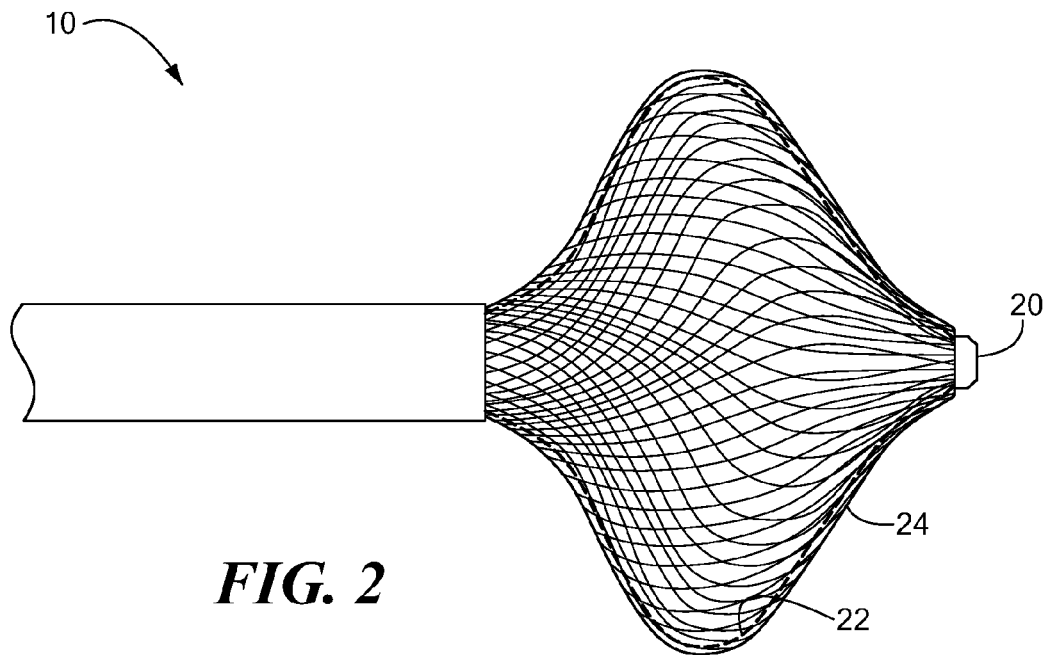
FIG. 2 shows an additional view of an embodiment of a surgical device in accordance with the present invention.

Referring now to FIGS. 1 and 2, an exemplary system including a surgical device 10 is illustrated for minimally invasive surgery. The system may include a console 12 and a surgical device 10, such as a multi-lumen catheter having an elongate body 14. The elongate body 14 may define a proximal portion and a distal portion, and may further include one or more lumens disposed within the elongate body 14 thereby providing mechanical, electrical, and/or fluid communication between the proximal portion of the elongate body 14 and the distal portion of the elongate body 14. For example, the elongate body 14 may include an injection lumen 16 and an exhaust lumen 18 defining a fluid flow path therethrough.

In addition, the elongate body 14 may include a guidewire lumen 20 extending along at least a portion of the length of the elongate body 14 for over-the-wire applications, where the guidewire lumen 20 may define a proximal end and a distal end. The guidewire lumen 20 may be movably disposed within at least a portion of the elongate body 14 such that the distal end of the guidewire lumen 20 extends beyond the and out of the distal portion of the elongate body 14.

The surgical device 10 of the present invention may further include an expandable element 22 at least partially disposed on the elongate catheter body. The expandable element 22 may include a balloon or other expandable structure, which may define a proximal end coupled to the distal portion of the elongate body 14 of the catheter, while further defining a distal end coupled to the tip portion and/or the distal end of the guidewire lumen 20. In addition, the expandable element 22 may have any of a myriad of shapes, and may further include one or more material layers providing for puncture resistance, radiopacity, or the like. The expandable element 22 may be in communication with the fluid injection and exhaust lumens of the surgical device 10 as described above, i.e., a fluid flow path may provide an inflation fluid, such as a cryogenic fluid or the like, to the interior of the expandable element 22.

The surgical device 10 of the present invention may further include a first leak detection element 24 coupled to the exterior of the distal portion of the elongate body 14, wherein at least a portion of the first leak detection element 24 is electrically conductive. The first leak detection element 24 may surround at least a portion of the expandable element 22, and may define a mesh or wire structure that is configurable into a plurality of geometric configurations, shapes, and or dimensions. As used herein, the term "mesh" is intended to include any element having an openwork fabric or structure, and may include but is not limited to, an interconnected network of wire-like segments, a sheet of material having numerous apertures and/or portions of material removed, or the like. In addition, the first leak detection element 24 may be constructed from a combination of elastic materials, non-elastic materials, and/or shape-memory materials, such as a nickel-titanium alloy or the like, for example.

Figure 3:
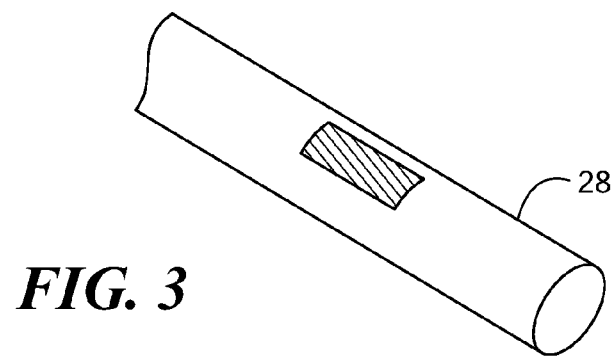
FIG. 3 depicts an embodiment of a leak detection element in accordance with the present invention.

The medical device of the present invention may further include a second leak detection element 26 in fluid communication with the fluid injection lumen 16, exhaust lumen 18, and/or the fluid path therethrough. The leak detection element may provide an electrically conductive electrode or the like disposed within the injection lumen 16, the expandable element 22, etc. In addition, the leak detectors may include an insulated length of wire 28, where a portion of the wire insulation has been stripped as shown in FIG. 3.

However, some catheters may include multiple conductors running within one or more lumens and electrical insulation on the conductors is necessary to avoid unwanted electrical connections and interferences. Many such catheters also contain uninsulated wires, for example as mechanical deflectors to alter catheter configuration, or for example as stiffening agents to alter catheter flexibility or pushability. However, if the pull wire (or other wire that is part of the leak detection circuit) contacts another uninsulated wire, electrode ring or other conductive element, a false leak detection signal could be generated. Accordingly, a form of insulation that provides mechanical and/or electrical insulation while allowing fluid conductivity may be desirable.

Figure 4:
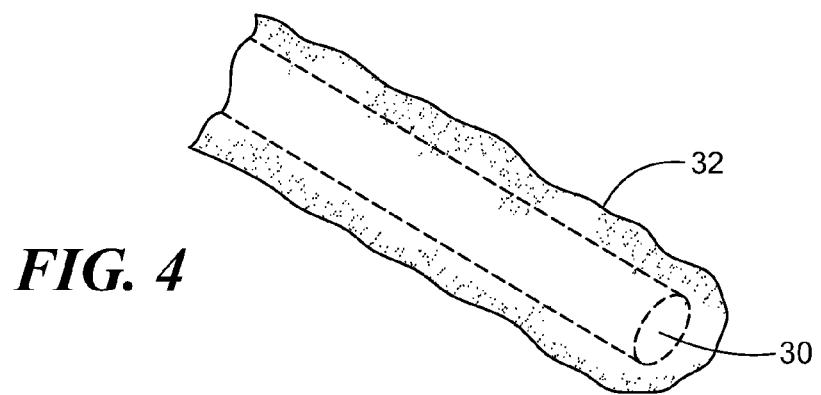
FIG. 4 illustrates another embodiment of a leak detection element in accordance with the present invention.

FIG. 4 discloses a wire 30 (such as a pull wire) that may be included in the leak detection circuit. The wire is covered with a porous material 32, such as a fabric, salt-depleted polymer, or laser drilled polymer, that provides mechanical insulation in the dry state by the physical bulk and separation of the porous material, which allows passage of ionic fluids to the thus insulated wire to complete the electrical leak detection circuit.

Again referring to FIG. 1, the catheter body of the surgical device 10 may have a proximal end that is mated to a handle 34, where the handle may include an element such as a lever or knob 36 for manipulating the catheter body and/or additional components of the surgical device 10. For example, a pull wire with a proximal end and a distal end may have its distal end anchored to the elongate body 14 at or near the distal end. The proximal end of the pull wire may be anchored to an element such as a cam 38 in communication with and responsive to the lever 36. The handle 34 can further include circuitry for identification and/or use in controlling of the ablation catheter or another component of the system.

The handle 34 may also include connectors that are matable directly to a fluid supply/exhaust and control unit or indirectly by way of one or more umbilicals for providing fluid communication with the elongate body 14. In the system illustrated, the handle 34 is provided with a first connector 40 that is matable with a co-axial fluid umbilical (not shown) and a second connector 42 that is matable with an electrical umbilical (not shown) that can further include an accessory box (not shown). The first and second connectors may provide fluid, mechanical, and/or electrical communication between portions of the surgical device 10 and the console 12.

The console 12 may house electronics and software for controlling and recording a surgical procedure, such as ablation, and may further control delivery of a liquid refrigerant under high pressure from a supply container 44, through an umbilical, to the elongate body. The console 12 can include an apparatus for recovery of expanded refrigerant vapor from the surgical device 10 and recompression of the vapor. Either or both of the surgical device 10 and the console 12 can be provided with detection devices that are in electrical communication with the console 12 and which may provide a signal output that can be representative of an event that indicates flow path integrity loss or a leak within a sealed portion of the surgical device 10 and/or console 12. For instance, the electrical impedance between the first and second leak detection elements may be monitored. If a bodily liquid enters the fluid flow path of the elongate body, the liquid will provide an electrical path between the first and second leak detection elements, creating a short detectable by circuitry in the console 12.

The console 12 can be configured to respond to signal output from the leak detectors and initiate a predetermined sequence of events, such as discontinuing refrigerant injection, changing the pressure within the system, and controlling removal of refrigerant from the catheter. The purpose and function of the leak detectors is better understood once another feature of the invention is introduced, namely, a vacuum pump 46, as shown in FIG. 1 in fluid communication with a catheter. The vacuum pump 46 is controllable to reduce the pressure within the exhaust lumen 18 of the catheter to provide a pressure ranging from a pure vacuum to a pressure just below a patient's blood pressure. For example, the vacuum pump 46 can maintain a selected pressure between 80 mm Hg and 0 mm Hg. The provision of reduced pressure within the return flow path of the elongate body significantly enhances patient safety because, should a leak occur, refrigerant will not squirt from the leak into the patient. Rather, bodily fluids in the treatment site will be aspirated into the elongate body whereupon they are sensed by the leak detection elements. In one mode of operation, when a leak is detected, the refrigerant injection may be turned off automatically while the vacuum remains in operation to ensure that no refrigerant enters the patient's body.

In an exemplary use of a system including the surgical device 10 of the present invention, the distal portion of the elongate body 14 of the surgical device 10 may be placed in proximity to a tissue region to be treated and/or thermally affected. Once in the desired position, a fluid, such as a cryogenic fluid, may be circulated through the fluid flow path of the surgical device 10. The flow rate, temperature, and other characteristics of the operation of the surgical device 10 may be monitored and/or controlled by the console 12. Under normal operating conditions, the first leak detection element 24 forms an "open-circuit" with the second leak detection element 26, or the first and second leak detection elements may comprise a portion of an impedance measurement circuit having known characteristics. Should the structural integrity and/or flow-path integrity fail, thereby allowing surrounding bodily fluids into the fluid flow path of the surgical device 10 and/or allowing fluid from the surgical device 10 to flow into the surrounding tissue region, the liquid will provide an electrical path between the first and second leak detection elements, thereby creating a short detectable by circuitry in the console 12, or causing a change in the impedance characteristics of the circuit including the leak detection elements. In such an event, a pre-determined sequence of events may be initialized, including terminating fluid flow to the surgical device 10 and/or varying the operation of the vacuum 46.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for leak detection in a medical device, comprising:
    circulating a fluid through a fluid flow path to an expandable element, the expandable element being substantially disposed within a mesh leak detection element;
    measuring an impedance between the mesh leak detection element and a second leak detection element in the fluid flow path; and
    discontinuing fluid flow in response to the impedance measurement.

2. A method for leak detection in a medical device, comprising:
    circulating a fluid through a fluid flow path to an expandable element, the expandable element being substantially disposed within a mesh leak detection element;
    detecting an electrical short between the mesh leak detection element and a second leak detection element in the fluid flow path; and
    discontinuing fluid flow in response to the detected electrical short.

3. The method according to claim 1, further comprising evacuating fluid from the surgical device.

4. The method according to claim 2, further comprising evacuating fluid from the surgical device.

* * * * *